United States Patent [19]
Brokish

[11] Patent Number: 6,127,608
[45] Date of Patent: Oct. 3, 2000

[54] DENT CORN INBRED 7791 DENT CORN HYBRID 6060BT

[75] Inventor: Harold A. Brokish, Champaign, Ill.

[73] Assignee: KWS SAAT AG, Einbeck, Germany

[21] Appl. No.: 09/225,915

[22] Filed: Jan. 5, 1999

[51] Int. Cl.[7] .............................. A01H 5/00; A01H 1/00; A01H 4/00; C12N 5/04
[52] U.S. Cl. ................. 800/320.1; 800/298; 800/275; 800/271; 435/410; 435/411; 435/412; 435/424; 435/430; 435/430.1
[58] Field of Search .................. 800/298, 320.1, 800/275, 271, 410–411; 435/412, 424, 430, 430.1

[56] References Cited

U.S. PATENT DOCUMENTS 5,684,227  11/1997  Bergemann ........................ 800/275

OTHER PUBLICATIONS

Phillip et al. Cell and tissue culture. Chapter 5. Cell/Tissue Culture and In Vitro Manipulation, 1988.

*Primary Examiner*—Lynette R. F. Smith
*Assistant Examiner*—Ousama Zaghmout
*Attorney, Agent, or Firm*—Townsend and Townsend and Crew LLP

[57] ABSTRACT

This invention is in the field of corn breeding, specifically relating to a dent corn inbred KW7791 and a resultant single cross dent corn hybrid designated as 6060Bt. Inbred KW7791 is especially bred for the north central United States and has demonstrated through the heterosis/hybrid vigor displayed in several single cross hybrids of which KW7791 is one of the parents, that it has superior general combining ability. Hybrid 6060Bt is a single cross hybrid developed by using KW7791 as one of the parents. Hybrid 6060Bt is a variety having superior agronomic performance that was especially bred for the north central United States.

12 Claims, No Drawings

DENT CORN INBRED 7791 DENT CORN HYBRID 6060BT

CROSS-REFERENCES TO RELATED APPLICATIONS

[Not applicable]

GOVERNMENT RIGHTS

[Not applicable]

FIELD OF THE INVENTION

This invention is in the field of corn breeding, specifically relating to a dent corn inbred designated as KW7791. Inbred KW7791 is an inbred that is especially bred by means of a backcross method for the north central United States and has superior general combining ability when compared to the next closest art forms resulting from this research project. 6060Bt is a commercial hybrid marketed for its performance in the north central Corn Belt. 6060Bt is a single cross hybrid resulting from using inbred KW7791 as one of the parents. The Bt trait in 6060Bt is donated from the inbred parent KW7791. The Bt gene in KW7791 is the Monsanto YIELDGARD gene. The patent application is based on the attributes of the inbred KW7791, not including the Bt gene, and the resulting hybrids.

BACKGROUND OF THE INVENTION

The goal of plant breeding in corn is to develop inbred parent lines that contribute various desirable traits to the hybrids in which they are used. These traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, stalk strength, root strength, ear retention, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produces a uniform population of hybrid plants that may be heterozygous for many gene loci. A cross of two plants each heterozygous at a number of gene loci will produce a population of hybrid plants that differ genetically and will not be uniform.

Corn plants (Zea mays L.) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations, the heterozygous condition gives way to homogeneous lines as a result of self-pollination and selection. Typically in the pedigree method of breeding, five or more generations of selfing and selection is practiced: F1; F2; F3; F4; F5, etc. These selfing generations are sometimes designated as S0, S1, S2, etc with S0 being an equivalent to F1 while S2 is an equivalent to F3, etc.

Backcrossing can be used to improve an inbred line or to develop a closely related new inbred line depending on the number of backcross generations and backcross methods employed. Backcrossing transfers a specific desirable trait from one inbred or source to an inbred that lacks that trait. This can be accomplished, for example, by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the nonrecurrent parent. After five or more backcross generations with selection for the desired trait, the progeny will be heterozygous for loci controlling the characteristic being transferred, but will be like the superior parent for most or almost all other genes. After the last backcross generation, the inbred line would be selfed to give pure breeding progeny for the gene(s) being transferred.

A single cross hybrid corn variety is the cross of two inbred parent lines, each of which has a genotype which complements the genotype of the other. The hybrid progeny of the first generation is designated F1. In the development of hybrids, only the F1 hybrid plants are sought. Preferred F1 hybrids are more vigorous than their inbred parents. This hybrid vigor, or heterosis, can be manifested in many polygenic traits, including increased vegetative growth and increased yield.

The development of a hybrid corn variety involves three steps: (1) the selection of plants from various germnplasm pools; (2) the selfing of the selected plants for several generations to produce a series of inbred lines, which, although different from each other, breed true and are highly uniform; and (3) crossing the selected inbred lines with unrelated inbred lines to produce the hybrid progeny (F1). During the inbreeding process in corn, the vigor of the lines decreases. Vigor is restored when two unrelated inbred lines are crossed to produce the hybrid progeny (F1). An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the F1 progeny. A double cross hybrid is produced from four inbred lines crossed in pairs (A×B and C×D) and then the two F1 hybrids are crossed again (A×B)× (C×D). Much of the hybrid vigor exhibited by F1 hybrids is lost in the next generation (F2). Consequently, seed from hybrid varieties is not used for planting stock.

Corn is an important and valuable field crop. Thus, a continuing goal of plant breeders is to develop consistent performing, high-yielding corn hybrids that are agronomically sound based on stable inbred lines. The reasons for this goal are obvious: to maximize the amount of grain produced with the inputs used and minimize susceptibility of the crop to environmental stresses. To accomplish this goal, the corn breeder must select and develop superior inbred parental lines for producing hybrids. This requires identification and selection of genetically unique individuals which in a segregating population occur as the result of a combination of crossover events plus the independent assortment of specific combinations of alleles at many gene loci which results in specific genotypes. Based on the number of segregating genes, the frequency of occurrence of an individual with a specific genotype is less than 1 in 10,000. Thus, even if the entire genotype of the parents has been characterized and the desired genotype is known, only a few, if any, individuals having the desired genotype may be found in a large F2 or S1 population. Typically, however, the genotype of neither the parents nor the desired genotype is known in any detail. An agronomically acceptable F1 hybrid will come from a cross between two superior inbred parental lines. There is no assurance that either of these parental lines will produce a superior hybrid when crossed with a different inbred parent line. Thus, the selection or combination of the two parental inbreds provides a unique hybrid that demonstrates characteristics and performance levels that differ from that obtained when either of the parents is crossed with a different inbred parent line.

Once the superior combination of two parental lines is determined by the testing and selection of the F1 hybrid, that F1 hybrid and the performance traits and characteristics of the hybrid can be indefinitely reproduced so long as the parental inbreds are maintained in their homozygosity and the quality and production procedures are accomplished to the purity standards determined by the seed industry regulation.

At Great Lakes Hybrids, Inc., there are approximately 100,000 pollinations made in each breeding nursery for each generation. Winter research stations are utilized in Puerto Rico and Chile to increase the developmental progress that can be accomplished in a given year. At various generations in the development of the inbred lines, they are crossed to an appropriate tester to made experimental hybrids. These experimental hybrids are tested in the appropriate areas of adaptation in the United States. The testing is conducted through the use of replicated test plots at several locations. Strip test plots are utilized as the hybrids approach commercial utilization.

SUMMARY OF THE INVENTION

This invention provides for inbred corn seed designated as KW7791 and having ATCC Accession No. PTA-599 This invention also provides for hybrid corn seed designated as 6060Bt and having ATCC Accession No. PTA-598 The invention also includes the corn plants produced by the seed of KW7791, 6060Bt and other plants resulting from all or part of the genetics of KW7791, with the exclusion of the Bt gene, and other resulting hybrids in which KW7791 is one of the parents. In addition, this invention provides for a corn plant having the physiological and morphological characteristics of the plant of inbred KW7791.

This invention also provides for tissue cultures of regenerable cells of a plant derived directly or indirectly from inbred KW7791 especially where the tissue regenerates into plants having all or essentially all of the important morphological and physiological characteristics of inbred KW7791. The plants regenerated from the tissue culture cells derived from inbred KW7791 are also a part of this invention.

Finally, inbred seed or hybrid seed produced utilizing the genetic contributions of a plant or plants derived from inbred KW7791 are expressly included in this invention.

DETAILED DESCRIPTION

According to the invention, there is provided a novel dent corn parent inbred, designated KW7791. Inbred KW7791 has been especially bred for the north central United States. In addition to matching or exceeding the phenotypes of the other segregates with regard to yield, vigor and the various commercially important agronomic traits, inbred KW7791 demonstated excellent general combining ability which was not apparent in the other segregates that were considered in the final level of selection. It is not normally expected to find one selection of a research project with excellent general combining ability in addition to strong, positive agronomic traits while all the other art forms resulting from the project fail in possessing strong agronomic traits and or exhibit only specific combining ability.

General combining ability is the ability of an inbred to exhibit genetic compatiblity with various sexual partners of varying pedigrees to provide an overall superior hybrid for each paired combination. The dominance is preferably across a wide variety of agronomically important traits. General combining ability is contrasted with "specific combining ability". Specific combining ability is present when the crossing of inbred A with inbred lines B through M provides a vigorous hybrid with inbred line B but agronomically poor vigor with inbred lines C through M.

General combining ability is important to the seed company as well as to the farming industry. An inbred with obvious positive agronomic traits and excellent general combining ability will most likely be utilized in more than one hybrid commercially. This provides the positive effects of this inbred's genetics to the farmers in more than one hybrid combination and most probably in more than one maturity.

This inbred, KW7791, is a homozygous inbred made by crossing the homozygous inbred parent line KW6691, designated as the recurrent parent, with the nonrecurrent parent genetics having a designation Mo17×(Mo17×(Monsanto R10232Bt×B73)). This was followed by four generations of backcrossing to the recurrent parent. Five generations of self pollinating followed the backcrossing to reach the desired level of homozygosity. Individual plant segregates were selected after each selfing generation and were planted in an ear to row method to maintain the individual identities of the selected segregates. Approximately 60 individual segregates were evaluated in the final stages of observation, testing, and selection. It was an unexpected event to observe that KW7791 was the only segregate to display excellent general combining ability. This general combining ability, (GCA) and heterosis pattern was not displayed by any of the closest forms of art which in this case would be the other segregates in the breeding project. The other segregates either did not display good general or specific combining ability or only displayed specific combining ability.

This invention thus relates to the seeds of inbred corn line KW7791, to the plants of inbred corn line KW7791 and to methods for producing a corn plant produced by crossing the inbred line KW7791 with itself or one or more other corn lines. This invention further relates to hybrid corn seeds and plants produced by crossing the inbred line KW7791 with another corn line.

Dent corn hybrid 6060Bt is a hybrid resulting from the cross of the inbred parents KW4678 and KW7791. In this case, KW7791 would be contributing fifty percent of the genetics to the resultant hybrid, 6060Bt.

Great Lakes Hybrids, Inc. has developed in its research program a unique art form in the inbred KW7791. In the presentation of data and information, the general combining ability of KW7791 is demonstrated by comparing it to the next closest art forms which are the recurrent parent, KW7691, and the next best segregate from the research project, designated as KW7691B.

The following data compares the performance of KW7791 in various hybrid combinations, to hybrids that are most closely related. Table 1 provides the agronomic traits of hybrids produced by crossing KW7791, its recurrent parent or KW7791's best sister line (KW7691B) to five different inbred lines. KW7691B was the best of 60 segregants resulting from a cross between KW7691 and Mo17x (Mo17x(Monsanto R10232BtxB73)).

The performance level demonstrated by the various hybrids when compared to the nearest art forms illustrates the exceptional general combining ability of KW7791. KW7791 hybrids were superior in all comparisons regardless of which other inbred parent it was combined with to form the respective hybrid. Dent corn hybrid 6060Bt is one of the hybrids resulting from the utilization of KW7791 as one of the parent inbreds.

DEFINITIONS RELATING TO TABLE 1

HYBRID. The single cross F1 combination produced by crossing two homozygous parent lines.
PEDIGREE. The names or designations for the homozygous parent lines used to form the Hybrid. The first parent line listed is the female parent followed by the male or pollinator parent.
LOC. The number of locations or test environments that were used in the collection of the data that is listed.
No. 2 YIELD. The shelled grain yield reported in bushels per acre based calculated at 15.5% moisture.
MOISTURE. The moisture is the actual percentage moisture of the grain at harvest.
POPUL. The population or plants per acre equivalent that are calculated from the physical count of the plants occupying the plot area.
%RL. The root lodging is the percentage of plants that root lodge; i.e., those that lean from vertical at an approximate angle of 30 degrees or more.
%SL. This is the percentage of plants that demonstrate lodging from natural forces. Lodging in this data is referred to as the breaking over of the plant below the upper ear node of attachment.
TW. Test Weight is the density weight of a standard bushel of shelled grain. This measurement is taken at the time of harvest.

DATA COMPARING KW7791 RELATED HYBRIDS

TABLE 1

| HYBRID | PEDIGREE | LOC | YIELD | MOIS | POPUL | % RL | % SL | TW |
| --- | --- | --- | --- | --- | --- | --- | --- | --- |
| 6060Bt | KW4678xKW7791 | 9 | 176.0 | 24.3 | 27,317 | 0.6 | 1.1 | 56.4 |
| 5849 | KW4678xKW7691 | 9 | 170.5 | 23.3 | 27,407 | 0.5 | 3.9 | 57.5 |
|  | KW4678xKW7691B | 9 | 171.8 | 24.2 | 26,941 | 0.4 | 3.9 | 57.8 |
|  | KW4632xKW7791 | 9 | 168.7 | 24.9 | 27,192 | 0.2 | 1.8 | 57.8 |
| 5962 | KW4632xKW7691 | 9 | 154.4 | 25.3 | 27,216 | 0.1 | 2.8 | 58.8 |
|  | KW4632Xkw7691B | 9 | 164.6 | 25.9 | 27,274 | 0.2 | 2.3 | 58.1 |
| 6565Bt | KW4363xKW7791 | 9 | 165.3 | 25.8 | 27,017 | 0.1 | 0.5 | 57.1 |
| GL591 | KW4363xKW7691 | 9 | 163.0 | 25.1 | 27,366 | 0.4 | 4.0 | 57.2 |
|  | KW4363xKW7691B | 9 | 157.2 | 26.1 | 26,990 | 0.2 | 1.2 | 56.9 |
|  | KW4610xKW7791 | 9 | 162.1 | 22.4 | 27,197 | 0.2 | 1.3 | 58.4 |
| 97535 | KW4610xKW7691 | 9 | 148.3 | 21.3 | 27,361 | 0.4 | 3.6 | 58.9 |
|  | KW4610xKW7691B | 9 | 156.6 | 23.1 | 26,889 | 0.0 | 1.7 | 58.6 |
|  | KW4720xKW7791 | 9 | 175.1 | 22.8 | 27,129 | 0.7 | 3.6 | 55.0 |
| 97539 | KW4720xKW7691 | 9 | 152.4 | 22.3 | 27,274 | 0.8 | 3.2 | 56.0 |
|  | KW4720XKW7691B | 9 | 162.0 | 24.0 | 27,287 | 1.0 | 3.0 | 56.2 |

The results in Table 1 demonstrate that KW7791 hybrids have superior performance when compared to the recurrent parent, KW7691, and when compared to the best of the other segregates from this research project. The best other segregate is identified as KW7691B. KW7791 hybrids were superior in all comparisons regardless of which other inbred parent it was combined with to form a hybrid. The superior performance of the KW7791 hybrids visually indicates the excellent general combining ability that was unique to this selection and that was not demonstrated by the other segregates in the project. 6060Bt was the most positive hybrid combination for the north central USA. Great Lakes Hybrids, Inc. selected this hybrid for commercialization based on the benefits the farmers gain from the positive agronomic performance as demonstrated in the data of Table 1. The data in Table 1 is from four row replicated plots in which the center two rows were harvested for data purposes. There were four replications per location for a total of 36 replications represented in the data.

ELECTROPHORESIS COMPARISONS

Isoenzymatic studies were conducted by Biogenetic Services, Inc located at 2308 6th Street; Brookings, S. Dak. Isozyme data were generated for Inbred KW7791 according to the procedures described in Stuber, C. W., Wendle, J. F., Goodman, M. M., and Smith, J. S. C., "Techniques and Scoring Procedures for Starch Gel Electrophoresis of Enzymes from Maize (*Zea mays L.*)," Technical Bulletin No. 286, North Carolina Agricultural Research Service, North Carolina State University, Raleigh, N.C. (1988).

In summary, the enzymatic components of partially purified cell homogenates are separated using conventional electrophoretic techniques (starch gels). The banded enzymes are then stained using substrate specific labeling techniques. The various enzymes are identified in Table 2. By convention, the dual numerical data reflects the diploid nature of the plants with each allelic form being randomly designated a number. Accordingly ADH1 is designated 11 or 12 with 11 representing a homozygous plant having identical isozyme forms (actually appearing as a single band) and 12 representing a heterozygous individual having two forms of ADH1. By comparison with the prospective parent lines, this analysis permits one to confirm the parentage of the tested individuals.

Table 2 lists the electrophoresis results for the dent corn inbred KW7791 and for the recurrent parent, KW7691. It is noted that both inbreds display the same pattern of banding, yet the yield, maturity and other agronomic traits measured in Table 1 indicate the superiority of KW7791 and the uniqueness of the inbred KW7791 that extends beyond the scope of the electrophoresis analysis.

TABLE 2

GENOTYPE ANALYSIS

| Inbred | AD1 | AC1 | AC4 | MD1 | MD2 | ID2 | PG1 | PG2 | GL1 | PM2 | PH1 | CA3 |
|---|---|---|---|---|---|---|---|---|---|---|---|---|
| KW7791 | 22 | 13 | 22 | 22 | 11 | 11 | 11 | 11 | 11 | 22 | 22 | 22 |
| kw7691 | 22 | 13 | 22 | 22 | 11 | 11 | 11 | 11 | 11 | 22 | 22 | 22 |
| Inbred | EN1 | ES1 | ES4 | G01 | G02 | HX2 | ID1 | MD3 | MD4 | MD5 | Mmm | PR1 |
| KW7791 | 33 | 22 | 33 | 22 | 11 | 33 | 22 | 11 | 11 | 11 | 11 | 22 |
| kw7691 | 33 | 22 | 33 | 22 | 11 | 33 | 22 | 11 | 11 | 11 | 11 | 22 |

Key:
AD1 = ADH1  AC1 = ACP1  AC4 = ACP4  MD1 = MDH1
MD2 = MDH2  ID2 = IDH2  PG1 = PGD1  PG2 = PGD2
GL1 = GLU1  PM2 = PGM2  PH1 = PHI1  CA3 = CAT3
MD4 = MDH4  MD5 = MDH5  Mmm = Mmm  PR1 = PRX1

Table 2 lists the electrophoresis identification for inbred KW7791. This table also reflects the close relationship of KW7791 and the recurrent parent, KW7691, which are components in the hybrids used in the presentation of the data in Table 1.

MORPHOLOGICAL TRAITS

Table 3 lists the morphological traits for dent corn inbreds KW7791 and KW7691. The two related inbreds were used in the data comparisons in Table 1 and Table 2 listed above. Table 3 indicates that there are differences that can be positively identified indicating that KW7791 has some unique morphological traits when compared to the next closest genotype. Table 3 also provides a morphological identification of several traits for inbred KW7791.

TABLE 3

| TRAIT | KW7791 | KW7691 |
|---|---|---|
| GDU 50% Pollen | 1416 | 1443 |
| GDU 50% SIlk | 1340 | 1364 |
| Plant Color | ML5GY6/6 | M5GY6/8 |
| Anther Color | 310RP4/4 | 310RPR4/8 |
| Silk Color | PALE GRN | SALMON |
| Leaf Orientation | 70 | 70 |
| Leaf Width | 8.2 | 9.1 |
| Number of Leaves | 4 | 4 |
| Tassel Type | 2 | 2 |
| Tassel Size | 8 | 8 |
| Tassel Length | 49.0 | 51.0 |
| Tassel Branch Number | 8 | 5 |
| Plant Height | 200 | 215 |
| Ear Height | 74 | 88 |
| Stalk Diameter | 20.3 | 23.2 |
| Shank Length | 8.0 | 8.2 |
| Husk Leaves | 40.0 | 94.0 |
| Ear Attitude | 3 | 3 |
| Glume Color | 15GY6/6 | 510RP4/4 |
| Glume Band Color | 2 | 1 |
| AnthocyaninBase | 3 | 3 |
| Anthocyanin in Nodes | NO | NO |
| Intacness Rating | 4 | 3 |
| Ear Type | CONICAL | CONICAL |
| Kernel Rows | 14–16 | 14–16 |
| Kernel Width | 8.0 | 10.0 |
| Kernel Length | 8.0 | 10.0 |

TABLE 3-continued

| TRAIT | KW7791 | KW7691 |
|---|---|---|
| Kernel Thickness | 4.4 | 5.0 |
| Cob Diameter | 22.8 | 24.0 |
| Cob Color | RED | RED |
| Weight of 100 Kernels | 19.0 | 33.8 |
| Grain Texture/Cap | 4/2 | 5/1 |
| Kernel Shape | TAPERED | TAPERED |
| Color of Kernel Cap | 3 | 3 |
| Color of Kernel Sides | 3 | 4 |

Table 4 lists the morphological traits for hybrid 6060Bt and for hybrid 5849 which is the next closest art form to 6060Bt. Hybrid 6060Bt is produced by crossing KW4678× KW7791. Hybrid 5849 is form by crossing KW4678× KW7691.

Table 4 indicates that there are differences that can be positively identified indicating that 6060Bt has some unique morphological traits when compared to the next closest genotype. Table 4 also provides a morphological identification of several traits for hybrid 6060Bt.

TABLE 4

| TRAIT | 6060Bt | 5849 |
| --- | --- | --- |
| GDU 50% Pollen | 1268 | 1241 |
| GDU 50% Silk | 1291 | 1268 |
| Plant Color | ML5GY7/6 | ML5G6/4 |
| Anther Color | 210RP5/4 | 210RP5/4 |
| Silk Color | PALE GRN | PALE GRN |
| Leaf Orientation | 75 | 70 |
| Leaf Width | 9.0 | 9.0 |
| Number of Leaves | 6 | 6 |
| Tassel Type | 3 | 3 |
| Tassel Size | 7 | 7 |
| Tassel Length | 55.0 | 54.0 |
| Tassel Branch Number | 11 | 9 |
| Plant Height | 125 | 125 |
| Stalk Diameter | 20.3 | 21.8 |
| Shank Length | 6.2 | 8.0 |
| Husk Leaves | 0.0 | 0.0 |
| Ear Attitude | 2 | 2 |
| Glume Color | 410RP4/4 | 210RP4/6 |
| Glume Band Color | 2 | 1 |
| Anthocyanin Base | 3 | 3 |
| Anthocyanin in Nodes | NO | NO |
| Intactness Rating | 2 | 4 |
| Ear Type | CONICAL | CONICAL |
| Kernal Rows | 16 | 16 |
| Kernel Width | 7.3 | 7.6 |
| Kernel Length | 13.0 | 12.7 |
| Kernel Thickness | 4.0 | 4.0 |
| Cob Diameter | 28.0 | 25.0 |
| Cob Color | RED | RED |
| Weight of 100 Kernels | 35.1 | 32.3 |
| Grain Texture/Cap | 4/2 | 3/2 |
| Kernal Shape | TAPERED | TAPERED |
| Color of Kernel Cap | 3 | 3 |
| Color of Kernel Sides | 4 | 4 |

DEFINITIONS FOR TABLE 3 AND TABLE 4

GDU 50% Pollen. Growing Degree Units from emergence of the plant to the stage at which 50% of the plants are shedding pollen.

GDU 50% Silk. Growing Degree Units from emergence of the plant to the stage at which 50% of the plants have exposed silks.

Calculation of Growing Degree Units for One Day $$GDUs = \frac{Temp.\,Max \times Temp.\,Min}{2} - 50$$

Enter the maximum temperature during the 24 hour period. If the maximum exceeds 86 degrees F., then enter 86. If the minimum temperature is less than 50 degrees F., then enter 50.

Plant Color. Color rating at flowering. SG=Soft Green, M=Medium Green ML=Medium Light Green, MD=Medium Dark Green, D=Dark Green Also, the Munsell Code is used.

Silk Color. Silk color is rated three days after the silks have fully emerged. 1=Pale Green, 2=Salmon, 3=Reddish, 4=Red, 5=Purpling, 6=Purple Leaf Orientation. Measured for the leaf above the upper ear. The measurement is in degrees from horizontal.

Leaf Width. The widest point of the leaf located at the upper ear measured in centimeters.

Number of Leaves. The physical count of the number of leaves above the upper ear node of attachment.

Tassel Type. 1=Free Standing, 5=Semi-open, 9=Shedding in the Whorl.

Tassel Size. 1=Small, 5=Medium, 9=Large

Tassel Length. Tassel length is measured from the top leaf collar to the tip of the tassel. The measurement is in centimeters.

Tassel Branch Number. This is the number of branches that originate from the main spike.

Plant Height. Measured in centimeters from the soil level to the tip of the tassel.

Ear Height. Measured in centimeters from the soil level to the upper ear node of attachment.

Stalk Diameter. Measured in millimeters in the center of the first full internode above the soil.

Shank Length. Measured in centimeters from the attachment to the stalk to the attachment to the ear.

Husk Leaves. Listed as a percent of plants demonstrating husk leaves.

Ear Attitude. Rating is taken at 65 days after 50% silk.
1=Upright, 2=Horizontal, 3=Pendent Glume Color. Color of the glumes of the tassel florets once the florets have emerged. Also, the Munsell Code is used.
1=Green, 2=Light Red, 3=Red, 4=Light Purple, 5=Purple Glume Band Color. Color of the glume bands on the tassel florets.
1=Green, 2=Light Red, 3=Red, 4=Purple Anthocyanin Base. Anthrocyanin presence in the brace roots.
1=Absent, 2=Faint, 3=Moderate, 4=Dark Anthocyanin in Nodes. Anthrocyanin presence in the nodes of the stalk.
Yes=Present, No=Not Present Intactness Rating. This is a visual rating that takes place at harvest time.
The scale is 1 to 9. 1=Best Ear Type. The shape of the dry ear before shelling. Cylindric or conical.

Kernel Rows. A physical count of the number of kernel rows at the midpoint of the ear.

Kernel Width. The kernels at the midpoint of the ear measured in millimeters

Kernel Length. The kernels at the midpoint of the ear measured in millimeters

Kernel Thickness. The kernels at the midpoint of the ear measured in millimeters Cob Diameter. The measurement is taken in millimeters at the midpoint of the cob.

Cob Color. Color of the dry cob when shelled.
1=White, 2=Pink, 3=Red, 4=Dark Red, 5=Other Weight of 100 Kernels. Weight in grams of a 100 kernel sample of shelled grain from an ear.

Grain Texture/Cap. This is a visual rating based on the hardness appearance of the endosperm and the formation of the dent in the kernel cap.
S=Soft, MS=Medium Soft, Med=Medium, MED HRD=Medium Hard, H=Hard
Dent Cap 1=Smooth, 2=Normal Dent, 3=Rough, 4=Sharp points Kernel Shape. Visual shape of the majority of the kernels on an ear.
1=Tapered 2=Peg(6 sided) 3=Square Color of Kernel Cap. Color of the cap or crown portion of the kernel.
1=White, 2=Light yellow, 3=Bright Yellow, 4=Dark Yellow, 5=Reddish, 6=Other Color of Kernel Sides. Color of the side of the kernel at the midpoint between the tip and crown.
1=White, 2=Light yellow, 3=Bright Yellow, 4=Dark Yellow, 5=Reddish, 6=Other

INDUSTRIAL APPLICABILITY

Corn is used as human food, livestock feed, and as raw material in industry. The food uses of corn, in addition to human consumption of corn kernels, include both products of dry-milling and wet-milling industries. The principal products of corn dry-milling are grits, meal, and flour. The corn wet-milling industry can provide corn starch, corn syrups, and dextrose for food use. Corn oil is recovered from the corn germ, which is a by-product of both dry-milling and wet-milling industries.

Corn, including both grain and non-grain portions of the plant, is also used extensively as livestock feed, primarily for beef cattle, dairy cattle, hogs, and poultry. Industrial uses of corn are mainly from corn starch in the wet-milling industry and corn flour in the dry-milling industry. The industrial applications of corn starch and flour are based on functional properties, such as viscosity, film formation, adhesive properties, and ability to suspend particles. The corn starch and flour have application in the paper and textile industries. Other industrial uses include de-icing products, plant fertilizer products and herbicide products.

Plant parts other than the grain of corn are also used in the industry. Stalks and husks are made into paper and wallboard and cobs are used for fuel to make charcoal. Cobs are also used as a carrier in other non-grain commercial products. The grain and the plant parts that are produced from the cultivation of 6060Bt can be utilized for human food, livestock feed, and as a raw material in the industry.

Inbred KW7791 can also be used to develop novel corn varieties. Standard breeding techniques can be used to isolate select qualities from inbred KW7791 for placement into new lines of inbred corn. Hybrid 6060Bt could also be utilized for the same purposes by using standard breeding techniques. Typical of these techniques is the recurrent and donor type breeding process. In addition, the inbred KW7791 and hybrid 6060Bt can be used as starting material to generate embryonic callus and cell suspensions. These cells can be used for a variety of known genetic techniques. Examples of the power of this new technology can be found in U.S. Pat. No. 5,134,074 entitled "Embryogenic callus and cell suspensions of corn inbred B73" and 5,484,956 entitled "Fertile transgenic *zea mays* plant comprising heterologous DNA encoding *Bacillus thuringiensis* endotoxin."

DEPOSITS

Applicants have made available to the public without restriction a deposit of at least 2500 homozygous seeds of Inbred KW7791 with the American Type Culture Collection (ATCC), Rockville, MD. 20852. The deposit was made on Sep. 1, 1999, and assigned Accession No. PTA-599.

Applicants have also made available to the public without restriction a deposit of at least 2500 F1 seeds of Hybrid 6060Bt with the American Type Culture Collection (ATCC), Rockville, MD. 20852. The deposit was made on Sep. 1, 1999, and assigned Accession No. PTA-598.

The seed deposited with the ATCC are taken from the same deposits maintained by Great Lakes Hybrids, Inc. at 972 County Road, 500 East, Ivesdale, Ill. 61851. These deposits of the Inbred KW7791 and of the Hybrid 6060Bt will be maintained without restriction in the ATCC depository for a period of 30 years, or five years past the most recent request, or for the effective life of the patent, whichever is longer, and will be replaced if the ATCC depository seed becomes nonviable during that time.

The claims defining the deposited plants are intended to encompass the deposited plant regardless of its origin or source. There are a variety of means to determine if a plant (test variety) is identical to the deposited plants. The most convenient is to simply make comparison to the extensive mophological information and genetic typing provided herein. When referring to plants as "identical", it is meant that the plants are so similar in phenotype and genotype that they would be classified as the same variety by a skilled breeder familiar with corn. Some minor variation within a corn population designated as a distinct variety is expected.

Test crossing with the deposited inbred plants is yet another means to determine identity between the claimed and test inbred variations. Crosses between and among the test and known inbred should provide identical populations of siblings once routine statistical tools are applied to accommodate for normal biological variation. This variation is that which is expected and found in any corn population which is defined as a variety by those of skill. Test crossing a common parent inbred with the claimed and with the test inbred variations should also provide identical populations of F1 sibblings within the parameters listed above.

Genomic typing of plants is a third means to determine identity and parental origin. Commercial laboratory services are available to perform such analyses. Methods include the use of the polymerase chain reaction (PCR) in generating random amplified polymorphic DNA (RAPD) and restriction fragment-length polymorphism (RFLP) linkage analysis. Another method is simple sequence repeats (SSR) also referred to as micro satellites.

What is claimed is:

1. An inbred corn plant identical in morphology and physioloy to a corn plant produced from seed having ATCC Accession No. PTA-599 (Inbred KW7791).

2. Seed producing the corn plant of claim 1.

3. A corn plant having as one of its parents, the inbred corn plant of claim 1.

4. Seed producing the corn plant of claim 3.

5. A corn plant identical in morphology and physiology to a corn plant produced from seed having ATCC Accession No. PTA-598 (Hybrid 6060Bt).

6. Seed producing the corn plant of claim 5.

7. A tissue culture of regenerable cells of a plant according to claim 1 wherein the tissue regenerates plants having all morphological and physiological characteristics of Inbred KW7791.

8. A corn plant regenerated from the tissue culture of claim 7.

9. A tissue culture of regenerable cells of a plant having at least 50% of its genome derived from the plant of claim 1.

10. A corn plant regenerated from the tissue culture of claim 8.

11. A method of producing corn seeds comprising the steps of:

(i) sexually crossing two corn plant varieties wherein at least one of two varieties is selected from the group consisting of: (a) an inbred corn plant identical in morphology and physiology to corn plants produced from seed having ATCC Accession No. PTA-599 (Inbred KW7791) and (b) corn plants having at least 50% of its genome identical to an inbred corn plant identical in morphology and physiology to corn plant produced from seed having ATCC Accession No. PTA-599 (Inbred KW7791); and, (ii) cultivating the sexually crossed corn plant to produce seed.

12. A method of claim 11 wherein the corn plant is an inbred corn plant identical in morphology and physiology to corn plants produced from seed having ATCC Accession No PTA-599 (Inbred KW7791).

* * * * *